United States Patent [19]

Ollivier et al.

[11] Patent Number: 4,859,373
[45] Date of Patent: Aug. 22, 1989

[54] PROCESS FOR THE PRODUCTION OF ALKANESULPHONIC ACIDS

[75] Inventors: Jean Ollivier, Arudy; Christian H. Lagaude, Pau; Hubert Baptiste, Lescar; Michèle Larrouy, Pau, all of France

[73] Assignee: Societe Nationale Elf Aquitaine (Production), Courbevoie, France

[21] Appl. No.: 148,867

[22] Filed: Jan. 27, 1988

[30] Foreign Application Priority Data

Feb. 25, 1987 [FR] France ............................... 87 02476

[51] Int. Cl.$^4$ ........................................... C07C 143/16
[52] U.S. Cl. .................................................... 562/119
[58] Field of Search ................................... 260/513 H

[56] References Cited

FOREIGN PATENT DOCUMENTS 83761    8/1971  German Democratic Rep. ................................. 260/513 H
48-22423 3/1973  Japan ................................ 260/513 H

OTHER PUBLICATIONS

R. E. Kirk et al., "Encyclopedia of Chemical Technology", vol. 13, "Stilbite to Thermochemistry", pp. 350–351, The Interscience Encyclopedia, Inc., New York, U.S.

Primary Examiner—Alan Siegel
Attorney, Agent, or Firm—Stevens, Davis, Miller & Mosher

[57] ABSTRACT

A process for the production of an alkanesulphonic acid by hydrolyzing in the heated state an alkanesulphonyl chloride. The process is preferably continuous. The hydrolysis reaction is initiated by the instantaneous use of energy released by the state change of one of the reagents internal to the system.

10 Claims, 1 Drawing Sheet

PROCESS FOR THE PRODUCTION OF ALKANESULPHONIC ACIDS

FIELD OF THE INVENTION

The present invention relates to production of alkanesulphonic acids. More particularly, it relates to production of these compounds from corresponding alkanesulphonyl chlorides.

BACKGROUND OF THE INVENTION

Alkanesulphonic acids and their salts have many industrial uses, which has prompted many producers to seek advantageous processes for production of these compounds. Indeed, the latter find uses as detergents, emulsifiers, and esterification catalysts. These compounds are especially useful for preparation of pharmaceutical products, as hardeners for certain resins, for example aminoalkyd resins and polyurethane resins, and as finishing agents for metals and the like.

Also known are several processes for production of alkanesulphonic acids, for example the oxidation of alkyl mercaptans or of dialkyl sulphides using nitric acid or oxygen, direct sulphonation of alkanes, treatment of alkanes with $SO_2$ and with oxygen, and action of chlorine on a mercaptan in the presence of water. Each process has its advantages and its shortcomings. The latter have led some industrialists to apply the known reaction of water with an alkanesulphonyl chloride:

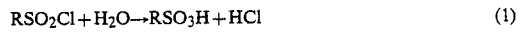

$$RSO_2Cl + H_2O \rightarrow RSO_3H + HCl \tag{1}$$

which may conveniently be performed with a good yield. See Kirk-Othmer Encyclopaedia, volume 13, pages 350–1954. This process is economically advantageous when an inexpensive source of $RSO_2Cl$ is available.

Such a hydrolysis process, as applied to methanesulphonyl chloride, is described in Japanese Pat. No. 48-22423 published in 1973. It consists in heating 1 mole of $RSO_2Cl$ with 1 to 1.5 moles of $H_2O$ at a temperature of 100° to 140° C. for several hours. This enables the acid $RSO_3H$ to be obtained with a yield exceeding 99.5%. However, as the reaction product is colored, the Japanese patent recommends that heating should be continued for a few hours, passing a stream of chlorine at the same time. Moreover, the latter may be introduced right from the beginning of the hydrolysis reaction, or alternatively only at the end of this reaction. According to the procedure applied, the preparation lasts on the whole for approximately 2 to 7 hours. Due to the action of chlorine, the product obtained is colorless.

However, in spite of the advantages this Japanese process has over other known techniques, it includes a constraint. This constraint is the use of a chlorine stream, and the subsequent need to drive off the excess of the latter by blowing an inert gas.

SUMMARY OF THE INVENTION

Given that it is currently possible to produce the starting material $RSO_2Cl$ quite economically, especially by one of the processes taught in French Publication Nos. 2,482,591 and 2,578,841, the hydrolysis process described above may prove to be very advantageous if it is possible to overcome the constraint relating to chlorine mentioned above. The investigations which led to the present invention were therefore directed towards this purpose. References cited above are hereby incorporated by reference.

DETAILED DESCRIPTION OF THE PROCESS

A first idea towards solving the problem came from the observation that the yellowing of the product becomes accentuated with time and becomes substantial especially towards the end of the hydrolysis which lasts for several hours. Therefore, if the hydrolysis could be achieved very quickly, it can be expected that no more color development will occur. Thus, the question raised is to find a way to strongly accelerate the hydrolysis reaction without a harmful increase in temperature. The answer was found following a careful study of the thermodynamics of the hydrolysis of alkanesulphonyl chlorides. Although this reaction is exothermic (approximately 53 kcal/mol for $R=CH_3$), the system $RSO_2Cl + H_2O$ demands a relatively high activation energy (22 kcal/mol when R is $CH_3$) to enable the hydrolysis to be initiated.

The inventive idea was therefore to provide the reaction mixture, right from the beginning, with the required activation energy without excessive temperature rise. This may be achieved by the instantaneous use of the energy released by the state change of one of the reagents. The embodiment which was found to be the most practical comprises providing to the starting alkanesulphonyl chloride the water required, in the form of steam, optionally superheated steam. The heat of liquefaction of it produces the activation desired. Once initiated, it then suffices to permit the reaction (1) to continue, while adjusting the temperature within appropriate limits, generally between 100° and 160° C.

This inventive concept, which has never been proposed in the past, was fully confirmed by experiment: it enabled the colorless product of excellent purity to be obtained with a high yield in less than 45 minutes. Therefore, this is 3 to 9 times quicker than can be obtained by the known process mentioned above. No injection of chlorine or of any other decolorizing agent is any longer required.

Thus, the process according to the invention, for the production of an alkanesulphonic acid by hydrolyzing the corresponding alkanesulphonyl chloride, is characterized in that water is provided in the form of hot steam, at the beginning of the reaction. After this, the reaction mixture is maintained at the appropriate temperature until the major part of the chloride is converted into alkanesulphonic acid. The hydrochloric acid formed is removed as it is formed.

When it is brought into contact with $RSO_2Cl$, the steam must be at a temperature at least equal to the boiling point of water at the operating pressure. Because the process conveniently may be carried out at atmospheric pressure, the steam is practically at 100° C., or above, in which case it is superheated. The injection of steam, which condenses on contact with the chloride, results in the agitation which is necessary. This is provided, at the same time as providing the $H_2O$ for the hydrolysis and activation energy for this reaction.

After this initial phase of the process, as the reaction initiated continues unaided, the temperature is adjusted preferably at values between 100° and 160° C. For $CH_3SO_2Cl$, the most favorable temperatures are between 125° and 145° C. and especially between 130° and 140° C. The residence time in the reaction zone generally is from 12 to 60 minutes and especially from 15 to 45 minutes.

An important factor in the new process is the proportion of water relative to the starting chloride. In contrast to the prior art, where 1 to 1.5 mol of $H_2O$ is preferably used per mole of $RSO_2Cl$, with the process of the invention, the best results are obtained when this ratio is 1.7 to 3.5 moles of $H_2O$ per mole of chloride, and preferably 2 to 3 moles of $H_2O$.

Although it is capable of being performed in a discontinuous manner, the process of the invention lends itself particularly well to continuous operation which is highly advantageous. In this case, it makes it possible to produce, for example, 3.5 kg of $RSO_3H$ per hour per liter of reaction volume.

In view of the ease with which the unconverted chloride can be separated, because $RSO_2Cl$ is of low or very low solubility in the aqueous $RSO_3H$ solutions obtained, it may be advantageous to limit the desired rate of conversion of chloride into acid to approximately 80 to 90%. This may be achieved extremely quickly, for example in approximately 20 min. Otherwise, it is possible to recycle the unconverted chloride into the reaction zone. Another solution comprises heating the remaining chloride in an additional reaction zone. The overall conversion may then approach 100%, at the cost of approximately doubling the total production time, which is quite acceptable.

The process of the invention may be applied to all alkanesulphonyl chlorides which can be mixed with water at 100° C. or above. It is highly useful for the production of $C_1$ to $C_{18}$, and in particular $C_1$ to $C_4$, alkanesulphonic acids.

The invention also comprises an installation for carrying out the new process described. It relates more particularly to an installation for the continuous production of alkanesulphonic acid.

The installation according to the invention, which comprises a reactor for maintaining, at an appropriate temperature, a mixture of water with an alkanesulphonyl chloride, means for the continuous introduction of these reagents into an inlet upstream of the reactor, means for the removal of the sulphonic acid formed, and means for the separation of HCl and the unconverted chloride, downstream of the reactor, is characterized in that the means for introduction comprise a mixer which is connected, on the one hand, to a source of alkanesulphonyl chloride and to a source of hot steam and, on the other hand, to the reactor itself.

The means for separation, downstream of the reactor, usually comprises a condenser for the moist HCl and a settler which enables the fraction of the initial chloride which has not been converted to be recovered.

In one variant, the bottom of the settler is connected to the inlet of the reactor and is equipped with means for recycling into the reactor the chloride recovered in the settler.

According to a particular embodiment of the invention, the settler is replaced with a secondary reactor, the bottom of which is connected to the sulphonic acid outlet of the main reactor. This secondary reactor is equipped with temperature regulating means, and it is used for completing the hydrolysis reaction which has not been completed in the main reactor.

BRIEF DESCRIPTION OF THE DRAWINGS

By way of non-limiting illustration, the drawings attached represent diagrammatically three embodiments of an installation according to the invention.

DETAILED DESCRIPTION OF APPARATUS

Figure 1:
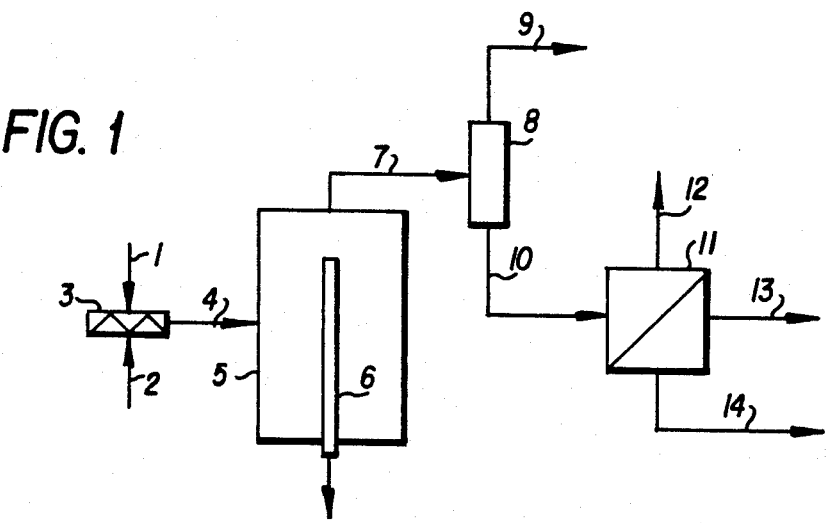
FIG. 1 is the diagram of an assembly containing a single reactor and a separator, without any recycling device for the unconverted chloride.

In the drawings, 1 denotes the inlet for alkanesulphonyl chloride and 2 that for steam which is at the boiling point of water at the pressure used in a mixer 3. From the latter, the reaction mixture, i.e. the chloride and water formed by the condensation of steam, passes through the pipe 4 into the main reactor 5.

The steam 2, preferably saturated, may be superheated. However, because it is convenient to work at atmospheric pressure or at a pressure slightly above it, the steam is generally at approximately 99° to 105° C.

The main reactor 5 is equipped with a conventional temperature regulating means, not shown on the drawing.

A solution of the alkanesulphonic acid formed flows out at the bottom of the reactor through the piping 6, whereas the volatile substances escape at the top, through 7, to be partially stopped in the condenser 8. The HCl gas leaves the condenser through the pipe 9, whereas the remaining constituents are directed through the pipe 10 into a settle 11. There, the remaining volatile substances, i.e. HCl and $H_2O$, escape through 12. The unconverted chloride, which has settled, is recovered at 13 and a small amount of aqueous alkanesulphonic acid solution leaves through 14. The residual $RSO_2Cl$ may, of course, be taken up at 13 and returned to the inlet 1 of the mixer 3.

Figure 2:
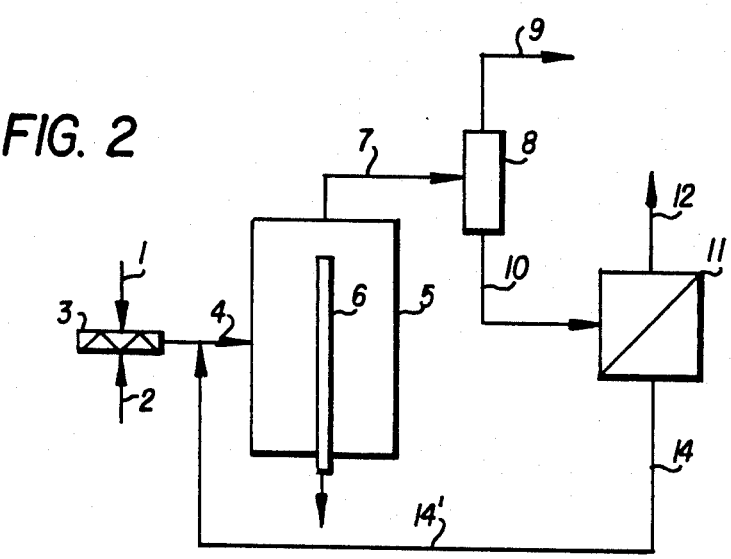
FIG. 2 shows a diagram similar to that in FIG. 1, but designed for recycling the unconverted alkanesulphonyl chloride.

The installation in FIG. 2 differs from that in FIG. 1 in that the chloride outlet 13 of the separator 11 is omitted, whereas the outlet 14 of the latter is connected, via a recycling pipe 14', to the inlet 4 of the reactor 5. Thus, the unconverted $RSO_2Cl$ is recycled together with a small amount of aqueous $RSO_3H$ which was entrained from the reactor via 7, 8, 10 to the separator 11.

Figure 3:
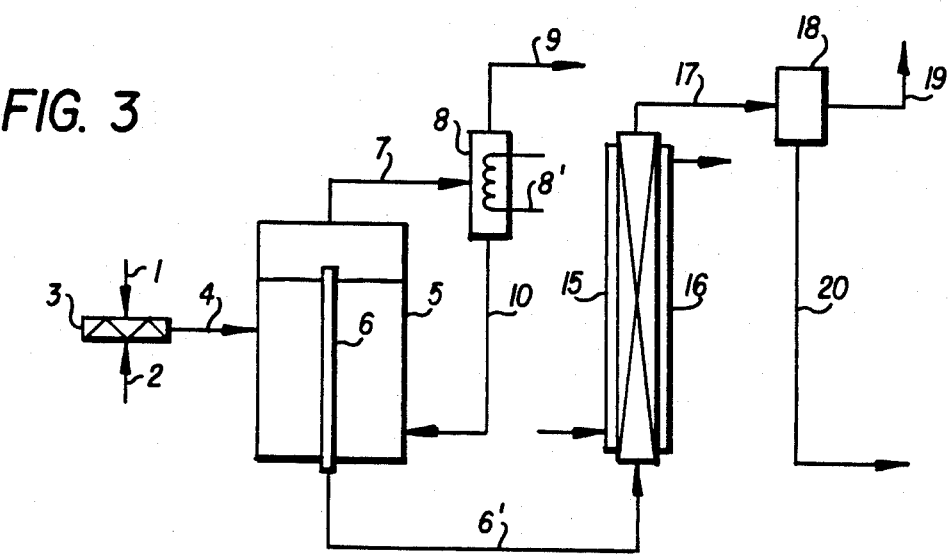
FIG. 3 shows the embodiment where an installation of the type of that in FIG. 1 contains a secondary reactor for completing the hydrolysis of the chloride, instead of the separator.

A third embodiment of the invention is shown in FIG. 3. Here, the sulphonic acid solution flowing out through 6 of the main reactor 5, is directed via a pipe 6' to the bottom of a secondary reactor 15 in which the hydrolysis of $RSO_2Cl$, which has not been converted in the main reactor 5, is completed. Means 16 are provided to adjust suitably the temperature in the secondary reactor 15, most frequently to a value of the same order as in 5, or slightly higher.

As the presence of HCl is unfavorable to the progress of hydrolysis (1), it is important to remove as much of it as possible from the mixture directed to the secondary reactor 15. For this reason, as for the components of FIGS. 1 and 2, the installation comprises the HCl degassing circuit 7, 8, 9. However, the coolant 8', used in the condenser 8, is supplied to stop the entire entrained amount of $RSO_2Cl$ and water. These substances are returned to the bottom of the main reactor 5 via the pipe 10'.

Another HCl separator 18 surmounts the secondary reactor 15 and communicates with it via a connection 17. HCl leaves at 19, whereas the sulphonic acid produced, containing water and very little HCl, flows out through 20.

EXAMPLES

The non-limiting examples which follow show the continuous preparation of $CH_3SO_3H$ by hydrolyzing $CH_3SO_2Cl$, according to each of the three embodiments described above.

In these examples, the mixer 3 is a 6 mm diameter tube. It has a volume of 10 ml. The main reactor 5 comprises a column which is 60 mm in diameter, 250 mm in height, and fitted with rings so that its useful volume is 200 ml.

The condenser 8 is at 27° C.

EXAMPLE 1

The installation is that in FIG. 1, which is used continuously under the following conditions:

| | |
|---|---|
| rate of supply of $CH_3SO_2Cl$ (at 1) | 847.3 g/h = 7.4 moles/h |
| rate of supply of steam at 102° C. (at 2) | 360 g/h = 20 moles/h | which amounts to 2.7 moles $H_2O$ per mole of chloride
temperature (at 5) . . . 150° C.
Results obtained:
  production of $CH_3SO_3H$ (at 6) . . . 585 g/h=6.09 moles/h, which amounts to 2.93 kg per liter of useful volume of the reactor/h,
  yield based on
  the chloride 82.3%
  recovery of HCl (at 9) . . . 60%
Residence time of the reaction mixture:
  in the mixer (3) . . . 45 seconds
  in the reactor (5) . . . 16 min 45 sec.
Thus, more than 82% of the starting chloride have been converted in 17 min. 30 sec, whereas in the prior art, several hours would have been required for this purpose.

EXAMPLE 2

The continuous preparation is carried out in the device in FIG. 2, i.e. the unreacted methanesulphonyl chloride being recycled.

| | | |
|---|---|---|
| rate of supply of fresh $CH_3SO_2Cl$ (at 1) | 834.7 g/h = | 7.29 mol/h |
| rate of supply of recycled $CH_3SO_2Cl$ (at 14'-4) | 125.9 g/h = | 1.10 mol/h |
| total rate of supply of $CH_3SO_2Cl$ | 960.6 g/h = | 8.39 mol/h |
| rate of supply of steam at 102° C. (at 2) | 260 g/h = | 14.45 mol/h | which amounts to 1.72 mol $H_2O$ per mole of chloride
Temperature (at 5). . . 136° C.
Results
  production of $CH_3SO_3H$ (at 6) . . . 702 g/h=7.32 mol/h
  which amounts to 3.5 kg per h per liter of useful volume;
  yield based on the chloride used (at 4) . . . 87.1%
  recovery of HCl (at 9) . . . 75% residence time of the reaction mixture in:

| | |
|---|---|
| the mixer (3) | 45 seconds |
| the reactor (5) | 14 min 30 sec. |
| total | 15 min 30 sec. |

The recycling of chloride therefore enables the sulphonic acid yield to be increased (87.1% as against 82.3% in Example 1) and this result to be achieved in 15 min 15 sec. It should be noted that during the first 45 seconds in the mixer (3), approximately 25% of the chloride introduced are already converted into sulphonic acid.

EXAMPLES 3 TO 5

The process is carried out with the unconverted chloride being recycled, in the equipment in FIG. 2, as in Example 2, but at lower temperature, 110°–114° C. varying the proportion of $H_2O$ relative to $CH_3SO_2Cl$.

| Example No | 3 | 4 | 5 |
|---|---|---|---|
| molar ratio $CH_3SO_2Cl/H_2$ | 2.84 | 1.73 | 1.5 |
| yield of $CH_3SO_3H$ | 80 | 72.2 | 52.7 |

It results therefrom that it is advantageous to use more than 2 moles of $H_2O$ per mole of chloride used. On the other hand, a comparison of Example 4 with Example 2 shows the large effect of temperature: for the same proportion of water of 1.73, the yield is 87.1% at 136° C. as against 72.2% at 110°–114° C.

EXAMPLES 6 TO 8

The trials are still carried out as in Example 2, with the device in FIG. 2, including the recycling of the unconsumed chloride. The process is carried out using a slightly longer residence time in reactor 5, viz. 17 min 30 sec. (plus 45 sec. in the mixer), which corresponds to a rate of supply of $CH_3SO_2Cl$ of 767 g/h (=6.7 mol/h). The proportion of $H_2O$ is 2 moles per mole of chloride
Results:

| Example No | 6 | 7 | 8 |
|---|---|---|---|
| temperature | 122°–130° | 137°–138° | 143°–148° |
| yield % | 93.7 | 94.3 | 93.2 |

Under the conditions mentioned above, the optimum temperature is therefore located at approximately 137° C.

EXAMPLES 9 AND 10

The continuous preparation of methanesulphonic acid is carried out in the device in FIG. 3, i.e. with a secondary reactor (15), described above, in addition to the main reactor (5). This additional reactor has a volume of 245 ml (height 40 cm). The operating conditions and the results are summarized below.

| Example No. | 9 | 10 |
|---|---|---|
| Rate of supply of $CH_3SO_2Cl$ g/h at 25° C. | 680 | 744 |
| Rate of supply of steam g/h at 100° C./ 1 bar | 220 | 252 |
| Molar ratio water:chloride | 2.05 | 2.15 |
| Residence time in: | | |
| mixer (3) | 0'45'' | 0'45'' |

-continued

| Example No. | 9 | 10 |
|---|---|---|
| reactor (5) | 19'15" | 17'32" |
| secondary reactor (15) | 22'00 | 22'00 |
| total | 42' | 40'17" |
| Temperature in the reactor (5) | 130° C. | 131° C. |
| Temperature in the secondary reactor (15) | 130° C. | 133° C. |
| Production in kg per h per 1 of total reaction volume | 1.2 | 1.3 |
| Yield % | 100% | 99.5% |

It is seen that the hydrolysis can be virtually complete if an additional reactor is used after the separation of HCl.

EXAMPLE 11 (COMPARATIVE)

The operations in Example 10 are repeated, but instead of saturated steam at 1 bar at 100° C., liquid water at 100° C. is introduced into the mixer (3).

In this case, the yield of methanesulphonic acid is 24%. To achieve a 99% yield, it was necessary to lower the rate of supply of $CH_3SO_2Cl$ from 744 to 180 g/h, i.e. to leave the mixture at 131°–133° C. for 166 minutes (instead of 40'17" in Example 10) and as a result, the product obtained was yellow. This illustrates the remarkable effect of using steam.

EXAMPLES 12 TO 14

In the same apparatus and following the same operating conditions as in Example 9, the sulfochlorides of ethane, 1-propane and 1-butane were hydrolized at the flow rate of 680 g/hr. The results thus obtained are summarized in the following table:

| Example | 12 | 13 | 14 |
|---|---|---|---|
| Sulfochloride of | ethane | 1-propane | 1-butane |
| Acid produced (g/hr) | 582 | 592 | 600 |
| Production (kg/hr/l) | 1.23 | 1.25 | 1.26 |
| Yield (%) | 100 | 100 | 100 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for the production of an alkanesulphonic acid comprising hydrolyzing, in the heated state, an alkanesulphonyl chloride, which process is continuous, characterized in that the hydrolysis reaction is initiated by prior use of required activation energy to the reaction medium wherein said activation is supplied in the form of latent heat of liquifaction of steam, by mixing a hot steam with said alkanesulphonyl chloride.

2. The process according to claim 1, wherein the steam is at the boiling point of water at system pressure.

3. The process according to claim 1, wherein proportion of steam used is from about 1.7 to 3.5 moles of $H_2O$ per mole of alkanesulphonyl chloride.

4. The process according to claim 3, wherein proportion of steam used is from about 2 to 3 moles of $H_2O$ per mole of alkanesulphonyl chloride.

5. The process according to claim 1, wherein use of the activation energy, especially mixing with steam, is carried out at a temperature in the vicinity of 100° C., after which the mixture is maintained at a temperature of between about 100° and 160° C.

6. The process according to claim 1, wherein the steam is at a temperature between about 99° and 105° C. and the mixture is maintained at a temperature between about 125° and 145° C.

7. The process according to claim 1, wherein hydrochloric acid is separated from reaction product, in the gaseous phase state from which unconverted chloride is separated by condensation, characterized in that the latter is recycled into the reaction zone.

8. The process according to claim 7, wherein after the separation of HCl, the reaction product is passed into a second reaction zone to complete the hydrolysis.

9. The process according to claim 1, wherein residence time for the mixture in the reaction is 12 to 60 minutes.

10. The process according to claim 1, wherein the residence time is 15 to 45 minutes.

* * * * *